United States Patent
Wu et al.

(10) Patent No.: US 12,287,770 B2
(45) Date of Patent: Apr. 29, 2025

(54) DYNAMIC RANDOM ACCESS MEMORY-BASED CONTENT-ADDRESSABLE MEMORY (DRAM-CAM) ARCHITECTURE FOR EXACT PATTERN MATCHING

(71) Applicant: University of Virginia Patent Foundation, Charlottesville, VA (US)

(72) Inventors: Lingxi Wu, Charlottesville, VA (US); Kevin Skadron, Charlottesville, VA (US)

(73) Assignee: University of Virginia Patent Foundation, Charlottesville, VA (US)

( * ) Notice: Subject to any disclaimer, the term of this patent is extended or adjusted under 35 U.S.C. 154(b) by 77 days.

(21) Appl. No.: 18/314,997

(22) Filed: May 10, 2023

(65) Prior Publication Data
US 2023/0385258 A1    Nov. 30, 2023

Related U.S. Application Data

(63) Continuation-in-part of application No. 17/462,836, filed on Aug. 31, 2021, now Pat. No. 11,776,594.

(60) Provisional application No. 63/364,444, filed on May 10, 2022.

(51) Int. Cl.
*G06F 16/22* (2019.01)
*G06F 16/2453* (2019.01)
*G06F 16/2455* (2019.01)

(52) U.S. Cl.
CPC ...... *G06F 16/221* (2019.01); *G06F 16/24532* (2019.01); *G06F 16/2455* (2019.01)

(58) Field of Classification Search
CPC .................................................. G11C 15/043
USPC ....................................................... 365/49.12
See application file for complete search history.

(56) References Cited

U.S. PATENT DOCUMENTS

| | | | |
|---|---|---|---|
| 6,487,101 B1 | 11/2002 | Ashbrook | |
| 11,882,218 B2 * | 1/2024 | Higo | H04L 9/3066 |
| 2016/0012102 A1 * | 1/2016 | Holley | G06F 16/242 |
| | | | 707/769 |
| 2016/0140243 A1 | 5/2016 | Adams | |
| 2022/0019665 A1 | 1/2022 | Perry | |

\* cited by examiner

*Primary Examiner* — Hoai V Ho
(74) *Attorney, Agent, or Firm* — Stanek Lemon Crouse & Meeks PA (57) ABSTRACT

Disclosed herein is a Dynamic Random Access Memory-Based Content-Addressable Memory (DRAM-CAM) architecture and methods relating thereto. The DRAM-CAM architecture can include a memory array, with the data organized into blocks including rows and columns. Input data can be converted into a format with first and second groups of columns. Each first group can correspond to one or more rows of the input data, and each second group can include one or more null columns. A query can be received and loaded into an available column of the second group, and pattern matching can be performed on the data to identify occurrences of elements defined by the query. The pattern matching can be performed concurrently on the first groups of columns and the available columns bit by bit. Results can include a count or location of each identified element.

19 Claims, 5 Drawing Sheets

DYNAMIC RANDOM ACCESS MEMORY-BASED CONTENT-ADDRESSABLE MEMORY (DRAM-CAM) ARCHITECTURE FOR EXACT PATTERN MATCHING

RELATED APPLICATIONS

This application is a continuation-in-part of U.S. patent application Ser. No. 17/462,836 (the '836 application), filed on Aug. 31, 2021, entitled "Scalable in Situ DRAM-Based Accelerators and Methods of Operating the Same." This application also claims priority to U.S. Provisional Patent Application No. 63/364,444, filed on May 10, 2022, entitled "Dram-Cam: General-Purpose Bit-Serial Exact Pattern Matching." Each of these applications is incorporated by reference in its entirety.

Any and all applications for which a domestic priority claim is identified in the Application Data Sheet of the present application are hereby incorporated by reference under 37 CFR 1.57.

STATEMENT OF GOVERNMENT SUPPORT

This invention was made with government support under Grant No. HR0011-18-3-0004 awarded by the Department of Defense/Defense Advanced Research Projects Agency (DARPA). The government has certain rights in the invention.

FIELD

Various embodiments of the disclosure relate to enhancing the performance of pattern matching operations in memory architectures through hardware and algorithm co-optimization. More specifically, the disclosure focuses on optimizing DRAM-based content-addressable memory systems for exact pattern matching workloads.

BACKGROUND

The exponential growth of digital data in recent years has resulted in an increasing demand for high-speed data processing and analysis. One of the most frequently used tasks in many applications is pattern matching. Exact pattern matching is a class of pattern matching that seeks to find occurrences of exact patterns in a given data set. However, exact pattern matching can be a computationally expensive task and can be a bottleneck in many applications.

Several solutions have been proposed to accelerate exact pattern matching, such as software-based algorithms and specialized hardware implementations. However, the performance of software-based solutions can be limited by the available computational resources, while specialized hardware solutions can be expensive and difficult to design and implement.

SUMMARY

Disclosed herein is a Dynamic Random Access Memory-Based Content-Addressable Memory (DRAM-CAM) architecture and methods relating thereto. The DRAM-CAM architecture can include a memory array, with the data organized into blocks including rows and columns. Input data can be converted into a format with first and second groups of columns. Each first group can correspond to one or more rows of the input data, and each second group can include one or more null columns. A query can be received and loaded into an available column of the second group, and pattern matching can be performed on the data to identify occurrences of elements defined by the query. The pattern matching can be performed concurrently on the first groups of columns and the available columns bit by bit. Results can include a count or location of each identified element.

Some embodiments of the present disclosure describe systems and methods for processing data using a DRAM-based content-addressable memory (DRAM-CAM) architecture. A system can include a memory array organized in a DRAM-CAM architecture, with raw input data stored in a plurality of blocks, where each block comprises several rows. The memory array can convert the raw input data into a standardized format featuring a plurality of columns arranged in an alternating pattern between first groups of columns and second groups of columns. The system can include a digital circuit that can concurrently execute pattern matching to identify occurrences of specific elements defined by a set of search criteria. Pattern matching can include accumulating a count of pattern matches and corresponding locations within the memory array.

In some embodiments, a method can include processing data using a DRAM-based content-addressable memory (DRAM-CAM) architecture. The method can include obtaining first data, which can include at least one of text or image information, and can be organized into a plurality of blocks, each block including a plurality of rows. The method can include storing the first data in a memory array of a DRAM-CAM architecture and converting the first data into a predefined format to form second data. The predefined format can include a pattern of alternating first groups of columns and second groups of columns, with each first group of columns corresponding to one or more rows of the plurality of rows of the first data, and each second group of columns including a predetermined number of null columns. The method can further include receiving a query, determining an available column of the second groups of columns, loading the raw query data into the available column of each second group of the second groups, performing pattern matching on the second data to identify occurrences of elements defined by the set of search criteria, and outputting results of the pattern matching. The pattern matching can be performed concurrently on the first groups of columns using a digital circuit that compares the first groups of columns and the available columns bit by bit. The method can further include accumulating a count of pattern matches and corresponding locations within the memory array, and the results can include the count and the location of each element identified in the second data.

In some embodiments, a method for processing data using a DRAM-CAM architecture can include obtaining first data, which can include at least one of text or image information and which can be organized into a plurality of blocks, each block including a plurality of rows. The method can include storing the first data in a memory array of a DRAM-CAM architecture, converting the first data into a predefined format to form second data. The predefined format can be characterized by a plurality of columns arranged in an alternating pattern between first groups of columns and seconds group of columns, wherein each first group of columns corresponds to one or more rows of the plurality of rows of the first data, and wherein each second group of columns includes a number of null columns. The method can include reorganizing the first data to form the second data by transforming each row of the plurality of rows of the block into one or more columns of the first groups of columns and interlacing the first groups of columns with the second group of columns to produce a set of interleaved columns in the second format for the block. The first/second data can be searchable responsive to a query.

The method described in the previous paragraphs can include one or more of the following steps or features. The number of null columns in each second group of columns can be equal to or greater than a number of columns in each first group of columns. The number of null columns in each second group of columns can be adjustable based on characteristics of the first data, and the reorganizing step can dynamically adjust the number of null columns based on the characteristics of the first data. At least one of the size or the number of null columns in each second group of columns can be based on timing parameters associated with the DRAM-CAM architecture. The step of converting the first data into the predefined format can be performed by a hardware data transposition unit implemented in hardware.

In some embodiments, a method for searching data in a DRAM-based content-addressable memory (DRAM-CAM) architecture can include receiving a query. The query can indicate a set of search criteria that defines first data as data to be searched and can define elements to be identified within the first data. The method can include loading query data into an available column of each second group of columns. The available column can be a null column in each of the second groups of columns. The second groups of columns can be stored alongside first groups in an alternating pattern between the first groups of columns and the second group of columns. The first group of columns can correspond to reference data to be searched. The method can further include performing pattern matching on the second data to identify occurrences of elements defined by the set of search criteria. The pattern matching can include accumulating a count of pattern matches and corresponding locations within the memory array. The method can include outputting results of the pattern matching.

The method of any of the previous paragraphs can include one or more of the following steps or features. The available column for storing query indications can be located in the same position in each of the second groups of columns. The pattern matching can be performed concurrently on the first groups of columns using a digital circuit that compares the first groups of columns and the available columns bit by bit or in a bit-parallel manner. Additionally, the method can include determining the available column of the second groups of columns, and the results can include the count and the location of each element identified in the second data. The pattern matching can be performed by a pattern matching engine implemented in hardware, and the count accumulation can be performed by an aggregation system implemented in hardware, configured as a Lookup Table (LUT) without pipeline, a LUT with pipeline, or a compressor tree.

The method of any of the previous paragraphs can include one or more of the following steps or features. The method can implement chip-level parallelism within the DRAM-CAM architecture to enable concurrent processing across multiple sub arrays of the memory chip, thereby enhancing pattern matching performance. When performing pattern matching on a text file using a set of search patterns including unique words, the method can aggregate hits for each input word within the memory array. Furthermore, the method can detect that all available columns in the second group of columns are occupied and designate a column within the second group of columns for overwriting, where the designated column is the available column. When performing pattern matching on an image file using a set of search patterns including 8-bit pixel patterns, the method can aggregate hits for each pixel pattern within the memory array. The pattern matching can include masking certain columns of the second data to selectively search for specific elements.

BRIEF DESCRIPTION OF THE DRAWINGS

The present disclosure is illustrated by way of example, and not limitation, in the figures of the accompanying drawings, in which like reference numerals indicate similar elements and in which.

DETAILED DESCRIPTION

Sieve is a processing-in-memory (PIM) architecture that utilizes DRAM technology to accelerate sequence matching in genomics. Sieve is described in the '836 Application, which has previously been incorporated by reference for all purposes. The concepts outlined in this application are compatible with and can be used in conjunction with any combination of the embodiments and features described in the '836 Application.

The Sieve architecture utilizes the parallelism and high bandwidth of DRAM to perform sequence matching at a significantly faster speed and with lower energy consumption compared to traditional software-based solutions. While the Sieve architecture has shown to improve the performance of genomic sequence matching, it may have limitations in its ability to handle other types of exact pattern matching workloads due to its specialized design.

The DRAM-CAM architecture disclosed herein extends the Sieve architecture with modifications to achieve a more general content-addressable memory (CAM) functionality. The disclosed DRAM-CAM architecture leverages the massive internal parallelism and high bandwidth of DRAM to perform exact pattern matching at a high speed and with low energy consumption. By enabling the processing of a wider range of exact pattern matching workloads, the disclosed DRAM-CAM architecture addresses limitations of the Sieve architecture and expands the use cases of DRAM-based processing-in-memory (PIM) architectures.

Figure 1A:
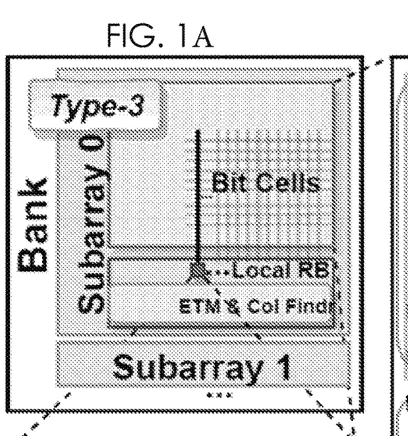
FIGS. 1A-1C depict aspects of a Type-3 Sieve architecture.
Figure 1B:
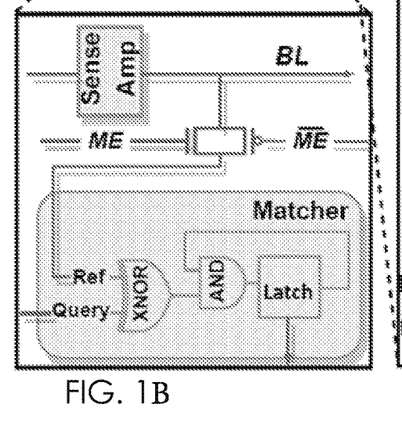
Figure 1C:
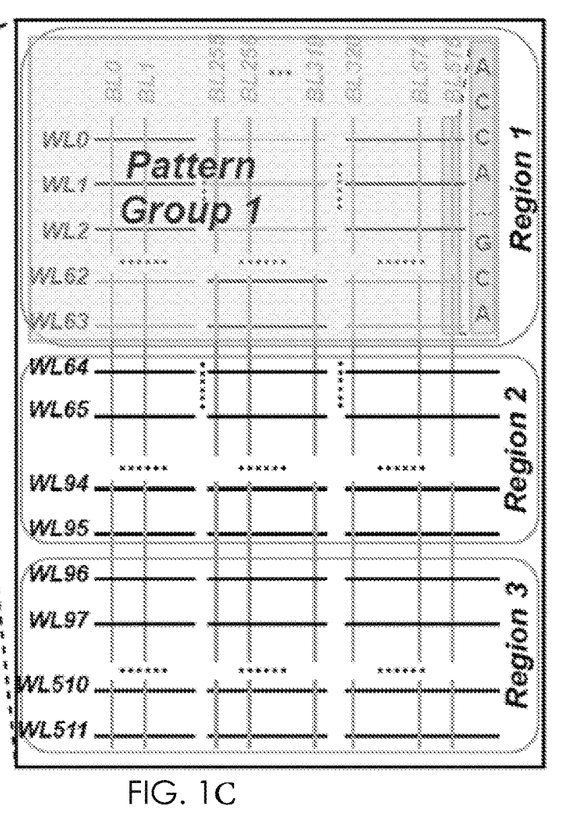

FIGS. 1A-1C depict aspects of the Type-3 Sieve architecture. FIG. 1A shows the incorporation of matching logic within each local row buffer. FIG. 1B illustrates the matcher logic, while FIG. 1C illustrates the partitioning of subarray bits into three regions for storing patterns (region 1), payload offsets (region 2), and payloads (region 3). The payloads are values associated with specific patterns that need to be retrieved.

The present disclosure relates to Sieve, which is a content-addressable memory (CAM) designed for efficient pattern matching. Specifically, the Sieve Type-3 architecture is illustrated in FIGS. 1A-1C and leverages subarray-level parallelism, with the pattern matching logic integrated into each local row buffer. The patterns are encoded in binary and transposed onto bitlines. The bit cells within each subarray can be divided into three regions (FIG. 1C). Region-1 stores the interleaved reference and query patterns, while Region-2 (optional) stores the Offsets to the starting address of payloads, allowing for location of the values associated with patterns (payloads). Region-3 stores the actual payloads. Data in Region-2/3 can be stored in conventional row-major format. In some cases, no physical modification is made to the bit cells.

Region-1 is further broken down into smaller pattern groups and a batch of query patterns can be replicated in each pattern group in the middle (shaded in FIG. 1C). Note each batch includes different queries, and it is replicated into different pattern groups. Queries can be processed in batches within different pattern groups due to the transmission delay of long wires inside DRAM chips. Broadcasting a query bit to all matchers during one DRAM row cycle may not be feasible. The exact size of a pattern group can be determined by the number of matchers that a query bit can reach in one DRAM row cycle, and the number of query patterns per batch can be determined by the chip's prefetch size. After a batch of query patterns finishes matching in a subarray, they can be replaced by a new batch via a series of write commands. Batching also minimizes the overhead of transaction (through PCIe) to Sieve, and amortizes the DRAM write commands of setting up queries to all pattern groups.

The matcher circuit, shown in FIG. 1B, can include an XNOR gate, an AND gate, and a one-bit latch, and operates on the digital output of a sense amplifier. The matcher can be bypassed or engaged by toggling the Match Enable signal. The XNOR gate checks if the reference bit and the query bit at the current base are equal. The bit latch stores the result of the XNOR operation, indicating if a reference and a query have been matched exactly up until the current bit position. The value in each bit latch can be set to 1 initially (default to match). The AND gate compares the previous matching result stored in the bit latch with the current result from the XNOR gate and updates the bit latch accordingly, capturing the running match progress bit-by-bit. When a row is opened, both query and reference bits are sent to sense amplifiers. A subarray controller then selects which query to process among the 64 queries in the subarray. Each pattern group has a 1-bit shared bus connecting all matchers. The selected query bit can be distributed to all matchers in a pattern group through this shared bus.

The Early Termination Mechanism (ETM) interrupts further row activation by checking if the entire row of latches is storing zeros. The matching process continues if at least one latch stores 1. To avoid broadcasting queries to every subarray, Sieve can utilize a coarse-grained indexing scheme that maps query patterns to a candidate subarray, which can reduce the number of subarrays that needs to be checked. The reference patterns in each subarray can be sorted alphanumerically from left to right, and then each entry in the index table can maintain an 8-byte subarray ID along with the binary values of the first and the last patterns at the respective subarray. The size of the index can grow linearly with the Sieve capacity rather than the length of patterns and can fit inside an LLC. The size of a such index table can stay under 2 MB even for a 500 GB dataset.

TABLE 1

Exact Pattern-Matching Workloads

| Application | Benchmark | Domain | Input |
| --- | --- | --- | --- |
| String Match | Phoenix | Text processing | Key and encrypted files |
| Histogram | Phoenix | Image processing | 1.4 GB bitmap image |
| Word Count | Phoenix | Text processing | 100 MB text file |
| Bitcount | MiBench | Automotive | 1,125,000 integers |
| Apriori | MineBench | Associative rule mining | 7,993,604 transactions, 1,000 unique items |

The present disclosure focuses on improving the performance of exact pattern matching workloads by implementing them on a DRAM-CAM architecture. The disclosed system processes a set of applications, including String Match, Histogram, Word Count, and Apriori, which are parallelizable with support from frameworks such as mapreduce or pthreads. String Match processes a key file that includes a list of plain English strings and an encrypted file that includes hashed (encrypted) values of English strings. String Match scrolls through keys in the key file and determines if any of them occur in a list of encrypted strings from the encrypted file. Histogram counts the frequencies of pixel values in the RGB channels of a bitmap image. Each pixel value can be stored as a 24-bit binary stream (8-bit per RGB component). Word Count generates the frequency of occurrence for each word in a large text file. Apriori is an associative-rule mining algorithm that iteratively builds a set of candidate itemsets and obtains their frequencies of occurrences in a database of transactions. Table 1 lists a set of applications that can be used for evaluating the performance of the disclosed DRAM-CAM architecture in handling various exact pattern matching workloads. The selected applications can be chosen from Table 1, with the exception of Vortex, which can be deprecated and not open source, and ReverseIndex, which may does not map well to DRAM-CAM.

Exact pattern matching is a computation kernel in applications ranging from text and image processing to data mining. A possible software implementation for such exact pattern matching kernels is to index reference patterns into a data structure such as a hash table, and matching is then simply a key lookup. However, the efficient execution of pattern matching on compute-centric platforms remains a challenge, due at least to its memory-bound nature. In particular, real-world applications can feature extremely large data sets, and consequently, the data structures do not fit in an on-chip cache, not even the last-level cache (LLC). Furthermore, the queries incur random accesses across large memory regions, which can lead to poor cache behavior and excessive data movement. Moreover, the computation per pattern lookup can be too small to mask the high data access latency, resulting in frequent processor stalls. An alternative can be to create a coarse-grained index that fits in the LLC, in which a key is mapped to a bucket of potential matches, and then linear or binary search is used within a bucket. However, this search can be expensive, and there can be poor temporal locality in which buckets are accessed.

To address these or other limitations, disclosed herein is an inventive concept for data-centric architectures that leverages content addressable memory (CAM) to address the limitations of conventional memory architectures. The disclosed inventive concept describes how to implement CAM functionalities inside DRAM, which offers several advantages over non-volatile memory (NVM) and SRAM based alternatives. First, NVM-CAM is less area-efficient. Even a highly compact 3T3R NV-CAM cell design based on PCM occupies 27F2, while the contemporary DRAM cell takes approximately 8F2. Second, NV-CAM is more energy-intensive, because it returns a matching result in one cycle by simultaneously activating all match lines in a CAM array (approximately 15 watt/chip). In comparison, the disclosed inventive concept activates DRAM rows sequentially within the indexed bucket, which consumes much lower energy for pattern comparisons (approximately 2 watt/chip). Furthermore, the lower power of each DRAM chip means high parallelism can be exploited, leading to superior throughput/watt (approximately 12×) of the disclosed inventive concept for DRAM-based CAM architecture. Finally, SRAM-CAM suffers from low capacity, since SRAM based CAM cells have lower density than both resistive CAM cells (e.g., STT-MRAM) and DRAM cells. Additionally, SRAM can be 10×-40× more power hungry than DRAM for the same capacity.

Disclosed herein is a content-addressable memory (CAM) architecture, DRAM-CAM, that is built on the Sieve, a recently-proposed processing-in-memory (PIM) accelerator designed for massively-parallel k-mer matching (searching for short DNA sequence patterns of size k). Sieve provides an average of 326×/32× speedup and 74×/48× energy savings over multi-core-CPU/GPU baselines for k-mer matching. While there are several DRAM-based PIM architectures capable of bulk exact pattern matching, Sieve serves as a better foundation due to its superior performance, using a column-wise data layout for patterns, allowing element-parallel, bit-serial matching (each bit position is checked across a large number of columns, or bitlines). The Sieve and SIMDRAM works showed that this offers better matching throughput than a traditional, row-wise data layout. This allows Sieve to integrate low-overhead bit-wise logic inside row buffers, coupled with subarray-level parallelism, to simultaneously compare thousands of patterns in short intervals without incurring expensive data movement. Although a similar in-situ approach has been explored in prior proposals such as DRISA, their multi-row activation-based processing scheme (also adopted in Ambit and SIMDRAM), which relies on charge-sharing, is more energy-intensive and slower than the sequential single row activation employed in Sieve, due to the overhead of massive copy operations involved to set up operand rows in the Bitwise group for pattern matching. Furthermore, column-wise data layout and single-row activation allows Sieve to exploit an Early Termination Mechanism (ETM) that prevents unnecessary DRAM row activation if all columns have encountered a mismatch. Therefore, even if the slow multi-row activation mechanism is replaced with the rapid issuing of timing-constraint-violating DRAM commands that leave multiple rows open to perform fast row-wide logic operations, as described in ComputeDRAM, Sieve still performs better by a large margin due to the benefit of ETM, which is not possible in a row-wise data mapping. Furthermore, combining ComputeDRAM with a vertical data layout is unlikely to outperform Sieve for pattern matching, because of the much larger overhead of setting up queries to the target subarrays.

The disclosed inventive concept relates to a general-purpose DRAM-CAM architecture for exact pattern matching. Representative benchmarks were dissected and a more general-purpose architecture was developed by extending the Sieve architecture. Population-count logic was added to address the need for knowing how many patterns matched, and a hardware transposition unit was developed to perform data transposition into the column-wise format in hardware instead of software. Hardware and software optimizations were also developed, such as chip-level parallelism. Evaluation of the DRAM-CAM architecture shows up to three orders of magnitude of speedup and energy reduction over CPU baselines.

DRAM-CAM Architecture

The disclosed DRAM-CAM can retain some or all of the core architectural designs of Sieve. In addition or alternatively, the disclosed DRAM-CAM can adopt the same or similar system integration. Furthermore, the disclosed architecture can incorporate several low-cost hardware components and runtime optimizations to enable support for a wider range of workloads and improve performance.

A population count logic (PCL) unit can be used to return the total number of matches for each query. The PCL can accumulate the number of ones from the row of latched bits in each participant subarray, which can then be aggregated at the controller level for the total number of hits. The PCL can be an important component in DRAM-CAM, as in many cases, aggregating hits for each query can account for a significant portion of the workloads. However, integrating the PCL at the resource-constrained subarray level can be challenging, as it can require processing a large bit vector in a timely fashion with minimal hardware overhead.

Figure 2:
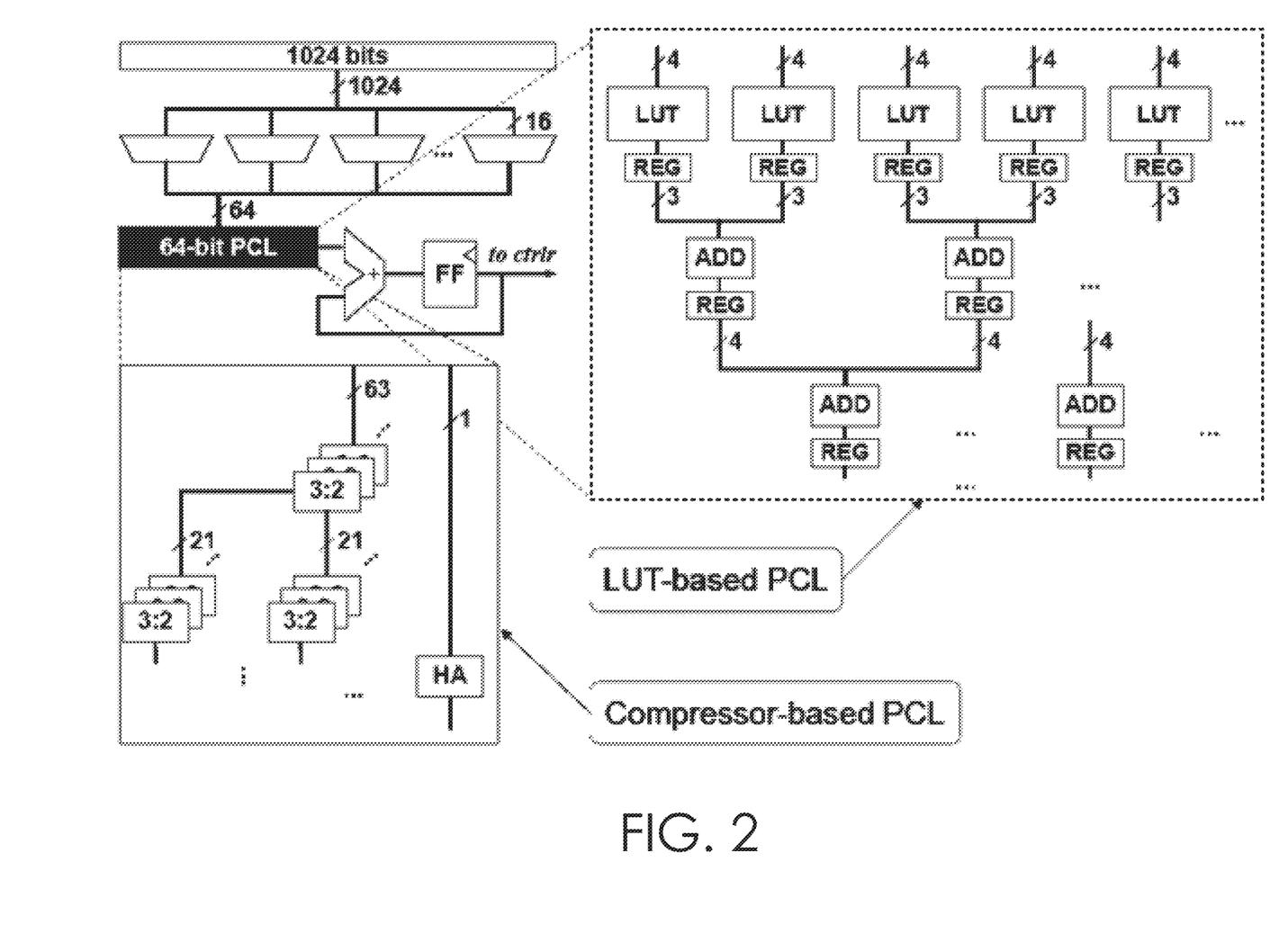
FIG. 2 illustrates an example design for the population count logic (PCL) unit according to the disclosed inventive concept.

FIG. 2 illustrates an example design for the population count logic (PCL) unit according to the disclosed inventive concept. The PCL can process 1024 bits by dividing them into chunks of 64 bits. To aggregate the number of is in each 64-bit chunk (the 64-bit PCL in FIG. 2), one of at least two options can be used: a lookup table (LUT) or a Wallace-tree architecture compressor tree circuit.

The LUT-based PCL can include 16 four-input lookup tables at the first level. Each LUT takes four bits from the latched row of bits of a subarray, and outputs the number of ones in binary. The remaining levels of this PCL are like an adder tree, which aggregates the number of ones from all LUTs. One optimization is to insert registers in between levels to form a pipelined PCL, which reduces the latency but increase the area and power overhead. The compressor-based PCL is documented. In short, it can include 57 3:2 compressors and 8 half-adders that are connected in ten cascading stages. The 3:2 compressor has the same truth table as a full adder. Each compressor processes a 3-bit binary pattern and represents the number of ones using its sum and carry bits.

If the reference patterns are reused across different executions, for example the k-mer sets built from a bacterial database that is only changing slowly, transposing the data in software is a one-time cost amortized over a long period of use. However, some workloads require input data to be transposed on the fly, and written to the DRAM-CAM prior to matching, which places the data transposition operation on the critical path. The disclosed inventive concept can integrate a simplified data transposition unit (DTU) from SIMDRAM into DRAM-CAM. The SIMDRAM DTU employs an 8 KB fully-associative cache to track if the addresses referenced in the instruction are reserved for PIM calculations, and includes two 4 KB (64 bits by 64 bits) SRAM buffers to support two-way data transposition from vertical to horizontal data layout and vice versa. DRAM-CAM, being a separate co-processor that supports only one kernel at a time and is non-cacheable, may require only one transposition buffer. DRAM-CAM's DTU works at a rate of transposing one cache line worth of data (512 bits) in one cycle. In some cases, a hardware DTU is at least 381.32× faster than a software one and adds an insignificant amount of execution time (<0.1% of execution time).

Sieve chips in a rank respond to queries in a lockstep manner due to the shared chip select signal (CS), a design carried over from a traditional DDR architecture. Chip-level parallelism (CLP) can be achieved by providing each chip with a dedicated chip select wire. Note this solution does not make each chip truly autonomous, because the data line (DL) still has to be shared inside a rank due to limited pin count.

Figure 3:
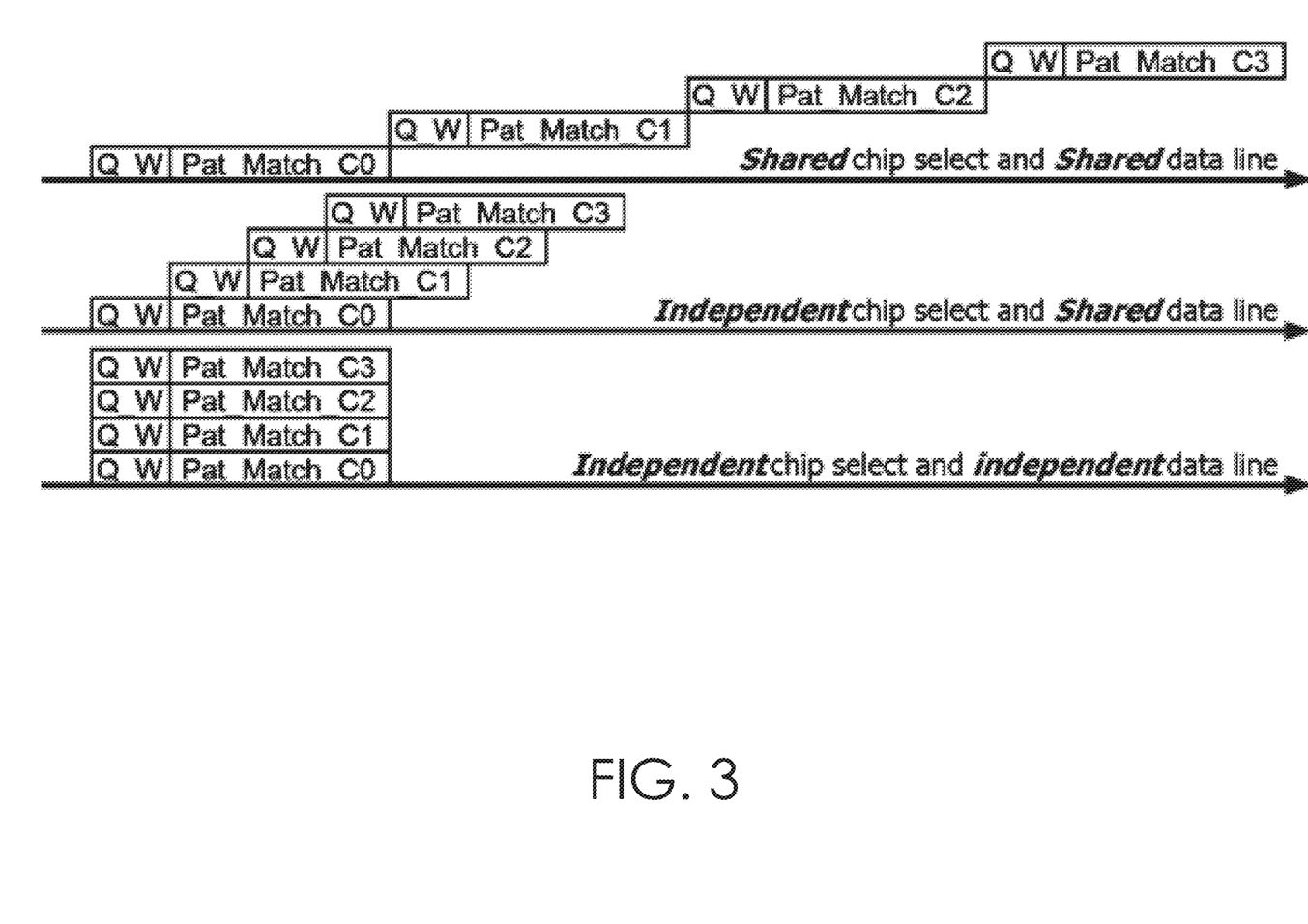
FIG. 3 illustrates a latency reduction from enabling Chip-level parallelism (CLP) of four chips in the same rank.

FIG. 3 illustrates a latency reduction from enabling CLP of four chips in the same rank. For each chip, the total matching latency includes the latency of writing the input query batch (Q_W) and the latency of pattern matching (Pat_Match_Ci). The top view shows the performance without CLP, and the bottom view shows the case where each chip is standalone with its own chip-select and DL (ideal). However, this system is expensive to build due to the demand for more high-frequency data pins. In accordance with the disclosed inventive concept, FIG. 3 illustrates a middle ground approach where each chip receives input queries once the shared data link (DL) is available, allowing for parallel processing of pattern matching while serialization of query input. The reduction in latency potential of the proposed Chip-Level Parallelism (CLP) is dependent on both chip and workload characteristics, with the ratio of Q_W to Pat_Match_Ci dictating its impact. Factors such as higher chip data bus bandwidth and shorter patterns can reduce Q_W, while higher row activations per query can increase Pat_Match_Ci. Q_W to Pat_Match_Ci is estimated to be between 1:7 and 1:10, demonstrating favorable potential for latency reduction. If Q_W is infinitely small, chip-level parallelism behaves identical to the ideal setup.

In some cases, a downside of CLP is that the number of entries of the index table can be increased, since chips may need to be indexed. However, the granularity of the indexing scheme can be adjusted if needed to keep the index within L2 capacity.

Figure 4:
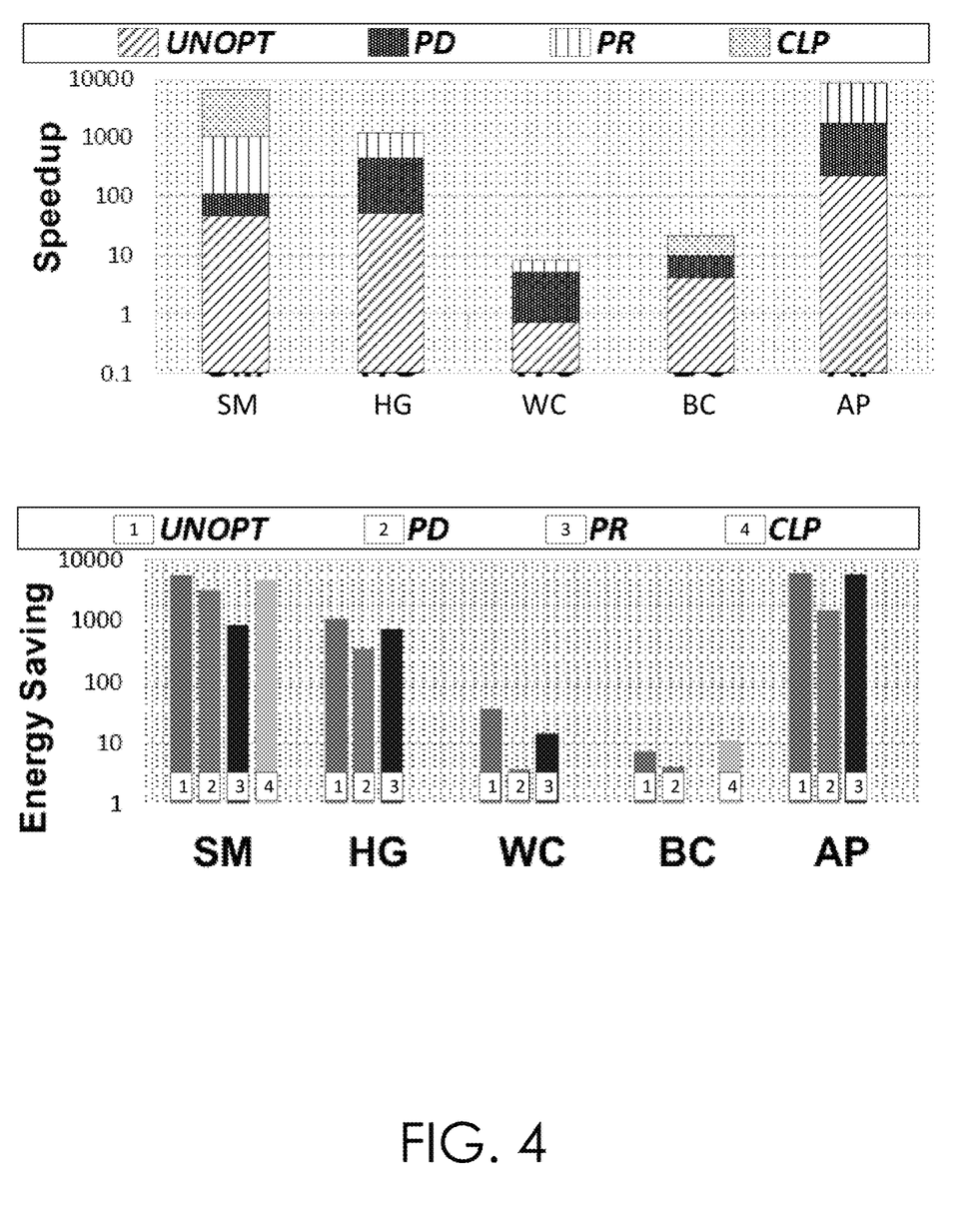
FIG. 4 illustrates a comparison between the disclosed Dynamic Random Access Memory-Based Content-Addressable Memory (DRAM-CAM) techniques and a central processing unit (CPU) baseline.

FIG. 4 illustrates a comparison between an example of the disclosed DRAM-CAM techniques and a CPU baseline. One optimization includes distributing reference patterns across subarrays, banks, ranks, and channels to maximize bank-level parallelism, and the other optimization involves replicating small reference pattern sets in unused subarrays to take advantage of subarray-level parallelism. Pattern replication provides better performance, resulting in a speedup ranging from 4.03× to 29.39×, while pattern distribution offers a speedup range of 22% to 7.35×, over an unoptimized pattern storage scheme.

To leverage the parallelism inside DRAM, one optimization can include distributing reference patterns to as many subarrays across different banks/ranks/channels as possible, which creates a higher chance of serving multiple matching requests concurrently and maximizes bank-level parallelism. Another optimization can include replicating small reference pattern sets multiple times by storing them in unused subarrays. Pattern replication allows applications leverage otherwise unused subarrays for pattern matching. Pattern distribution (PD) offers 22% to 7.35× while pattern replication (PR) offers 4.03× to 29.39× speedup over an unoptimized pattern storage scheme (FIG. 4). PR generally offers better performance than PD, because it allows DRAM-CAM to utilize subarray-level parallelism on top of bank-level parallelism.

While some kernels map to DRAM-CAM naturally, such as String Match (SM) and Bitcount (BC), others may not be so straightforward and require algorithmic changes. Histogram (HG) and Word Count (WC) differ most from their CPU counterparts, where the input images or text files are transposed and stored into DRAM-CAM prior to the matching process. Then a standardized input set such as all 8-bit pixel patterns or unique English words can be passed as input to aggregate hits. For the Apriori (AP), a partial or the entire transaction database can be transcribed using one-hot encoding, with each column representing a transaction and each row representing an item. To check if a candidate itemset is a subset of a transaction, the ith row corresponding to the ith 1 of the bit vector can be opened.

TABLE 2

Mapping exact matching kernels onto DRAM-CAM

| Benchmark | Index | ETM | PCL | DTU | CLP | Input | Payloads | DRAM-CAM patterns | DRAM-CAM computing |
|---|---|---|---|---|---|---|---|---|---|
| String Match | Yes | Yes | No | No | Yes | Key file | None | Encrypted file | Search keys in the encrypted file |
| Histogram | No | Yes | Yes | Yes | No | 8-bit pixels | None | Image binary pixel values | Aggregate hits for each pixel pattern |
| Word Count | No | Yes | Yes | Yes | No | Unique words | None | Words from text file | Aggregate hits for each input word |
| Bitcount | Yes | No | No | No | Yes | 32-bit binaries | Num of set bits | 32-bit binaries | Retrieve number of set bits |
| Apriori | No | No | Yes | No | No | Itemsets as bit vectors | None | One-hot encoded transactions (bit vectors) | Check if candidate itemsets are subsets of transactions by opening rows |

Table 2 shows details of mapping each kernel onto DRAM-CAM. In some cases, matching the patterns in reverse order can provide a good or the best way to utilize Early Termination Mechanism (ETM) in the context of natural language (such as Word Count), owing to significant prefix overlapping. This finding has been summarized in Table 2, which presents more details on the mapping of each kernel onto DRAM-CAM.

TABLE 3

Effect of chip-level parallelism.

|  | LUT no Pipeline | LUT Pipeline | Compressor Tree |
| --- | --- | --- | --- |
| Area (nm2) | 201 | 554 | 148 |
| Delay (ns) | 0.76 | 0.34 | 0.84 |
| Power (uW) | 0.03 | 0.06 | 0.02 |

Table 3 presents performance characteristics for the population count logic (PCL). The compressor-based PCL has lower area and power, while the pipelined LUT-based PCL is the fastest. The disclosed DRAM-CAM architecture includes fitting the PCL in the center strip of each DRAM chip, and each PCL is time-shared among subarrays of a bank. This setup may increase the latency slightly. Decoupling CS signals to enable chip-level parallelism can require negligible hardware changes. For the data transposition unit, the primary component can be a 4 KB SRAM buffer. In some cases, its area is estimated to be 0.015 $mm^2$, and it consumes 2.22 uW power.

FIG. 4 reports the speedup and energy saving over a CPU baseline of various DRAM-CAM configurations, including the performance of an unoptimized (UNOPT) setup and the benefit of three optimizations, pattern distribution (PD), pattern replication (PR), and chip-level parallelism (CLP). For applications that need population count logic, the fastest PCL setup was selected, namely LUT with pipeline. Several conclusions can be draws. First, the optimizations can be highly effective when the reference pattern set is small, at least because it can be distributed and replicated many times to leverage the massive internal parallelism of DRAM structure. Additionally, chip-level parallelism offers approximately 2.9× speedup when applicable, but it may not help when a query needs to visit all subarrays to aggregate hits. Second, String Match (SM) shares the most similarities with k-mer matching, therefore it maps naturally to DRAM-CAM, and benefits the most from such accelerator. Third, Word Count (WC) map can experience modest speedup. In some cases, the unoptimized DRAM-CAM is 1.5× slower than CPU. There are at least two reasons: (1) long string patterns and high match rate cause frequent and long sequences of DRAM row openings, and (2) a large input set (reference patterns) that limits the optimization potential. This is in contrast to Apriori (AP) which also stores large reference sets and long patterns. However, each query in Apriori can open a few rows (<10). Fourth, DRAM-CAM outperforms the CPU implementation of Bitcount (BC), which stores a small lookup table (256 entries of 8-bit binary patterns) in the L1 cache, whereas DRAM-CAM stores a much larger lookup table (32-bit binary patterns) and can thus sustain much larger throughput. The baseline DRAM-CAM (UNOPT) tends to show the best energy efficiency, at least because the dynamic power consumption of DRAM-CAM depends on the number of banks that are used for pattern matching, and the UNOPT setup uses a small percentage (0.7%-50%) of banks, resulting in up to 126.39× lower power than the CPU baseline. PD shows worse energy saving than UNOPT, even though it offers better speedup, because UNOPT uses all subarrays of a smaller set of banks, but leverages subarray-level parallelism (SALP) to its full potential, thus making up the performance loss due to increased bank conflicts. It is noted that PD tends to use a smaller number of subarrays from a larger set of banks, resulting in a sublinear speedup with respect to the number of banks utilized.

PR may show better energy saving than PD, except for the SM benchmark, by exploiting more SALP. SM has a small input set, and PD utilizes two banks (low power). PR offers 16× speedup, but needs 128 banks, However, HG, WC, and AP have larger data sets, and PD can include the same amount of banks as PR, meaning they have similar dynamic power consumption. Since PR significantly reduces the execution time of those benchmarks, it offers better energy efficiency for those benchmarks. CLP may increase power consumption minimally, but the performance improvement can be significant, so the energy savings approach or surpass UNOPT.

This disclosed inventive concept presents an extension of the Sieve DRAM-based PIM architecture with low-overhead features, enabling a wider range of exact pattern matching workloads with significant energy reduction over CPU. The UNOPT DRAM-CAM offers 62.99×/207.98× average/max speedup, and 2552.75×/6174.77× average/max energy savings, compared to a CPU. Further optimizations provide up to 2467.09×/6217.42× average/max speedup, and 2262.78×/5888.30× average/max energy savings.

Figure 5:
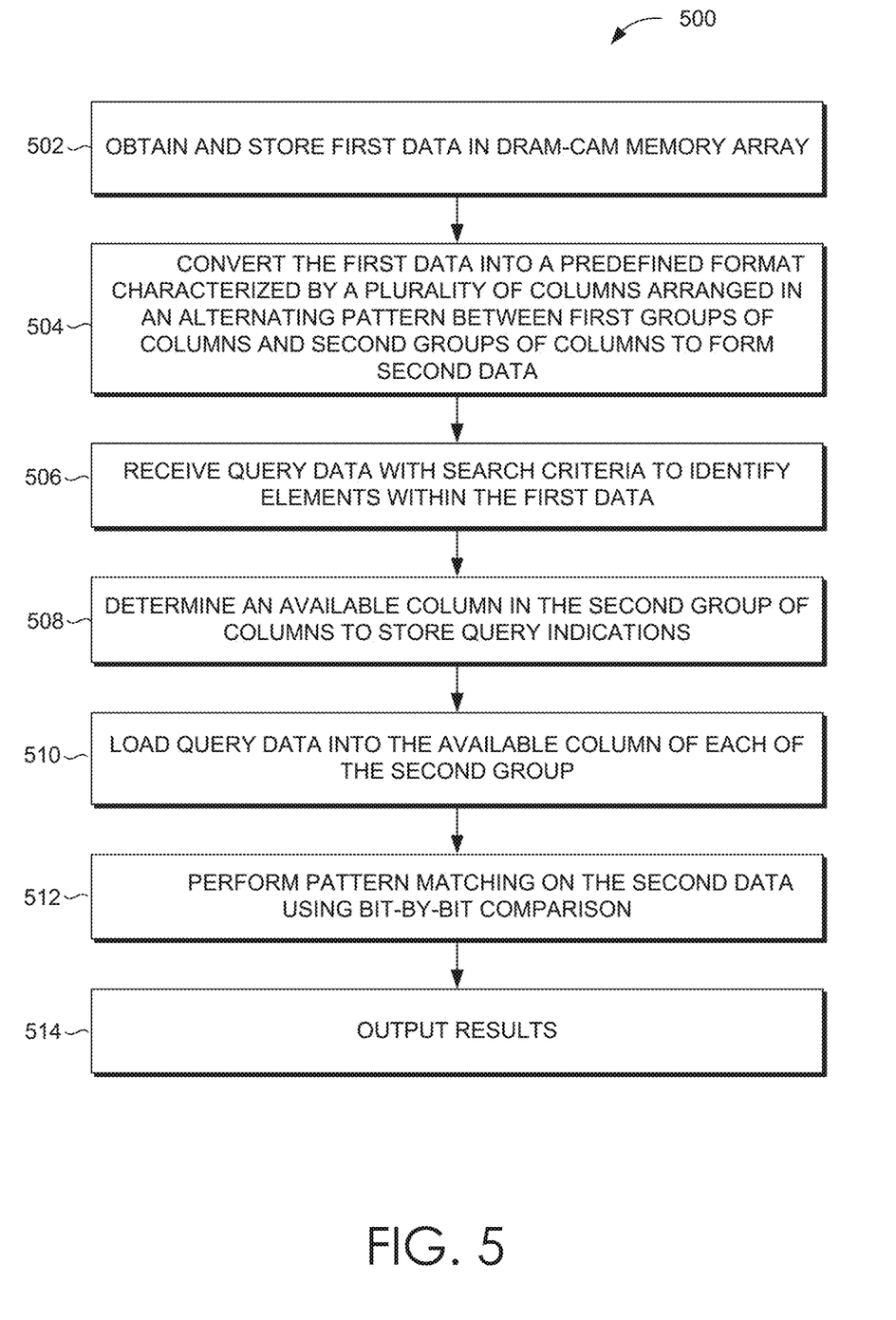
FIG. 5 is a flow diagram illustrative of an embodiment of a routine implemented using a DRAM-CAM system.

FIG. 5 is a flow diagram illustrative of an embodiment of a routine 500 implemented using a DRAM-CAM system. Although described as being implemented by a DRAM-CAM system, it will be understood that one or more elements outlined for routine 500 can be implemented using any combination of software or hardware. For example, one or more steps may be performed in hardware by the Population Count Logic (PCL) unit and/or the Data Transposition Unit (DTU), as described herein. Thus, the following illustrative embodiment should not be construed as limiting. Furthermore, fewer, more, or different blocks can be used as part of the routine 500. For example, in some cases, the routine 500 may only include those steps relating to storing the first data (e.g., steps 502 and 504). In addition or alternatively, in some cases, the routine 500 may only include those steps relating to receiving and performing a query (e.g., steps 506, 508, 510, 512, and/or 514).

At block 502, the DRAM-CAM system obtains and stores first data in a DRAM-CAM memory array. The first data can include raw input data such as text or image information. The first data can be organized into a plurality of blocks. Each block can include a plurality of rows, where each row can represent a specific segment of the input data. The memory array of the DRAM-CAM architecture can store the first data, facilitating subsequent processing and searching operations in an efficient and structured manner.

In some cases, the organization of the first data into blocks and rows offers a systematic approach to data storage and retrieval. By arranging the first data in a well-defined structure, the DRAM-CAM architecture can enhance the efficiency of data processing and retrieval, contributing to the overall performance of the DRAM-CAM system. This structured organization of the first data can provide a foundation for the subsequent data conversion, query processing, and pattern matching steps, allowing for more effective searching and identification of specific elements within the data.

At block 504, the DRAM-CAM system converts the first data into a predefined format characterized by a plurality of columns arranged in an alternating pattern between first groups of columns and second groups of columns. In some cases, this conversion may be referred to as normalizing the first data. The predefined format can allow for efficient data searching and pattern matching in the memory array. In this predefined format, a plurality of first groups of columns can be formed, where each first group corresponds to one or more rows of the plurality of rows of the first data. In addition, a plurality of second groups of columns can be created, with each second group including a number of null or empty columns that can be populated with search/query data. The columns of the second group can be referred to as bit lines, as described herein. The same column in each second group can correspond to the same query data, enabling efficient pattern matching.

The transformation of each row of a block of the first data into one or more columns of the first groups of columns can occur, followed by interlacing the first groups of columns with the second group of columns to produce a set of interleaved columns in the second format for the block. In some cases, the set of interleaved columns in the second format is referred to as second data. The number of columns in the first or second groups can be dynamic or predetermined, based on various factors such as the characteristics of the first data or timing parameters associated with the DRAM-CAM architecture. For example, the number of null columns in each second group of columns can be equal to or greater than the number of columns in each first group of columns. As another example, in some cases, the number of null columns in each second group of columns can be dynamically adjusted based on the characteristics of the first data or timing parameters associated with the DRAM-CAM system. The conversion can be performed by a hardware data transposition unit implemented in hardware, as described herein, thereby streamlining the process and enhancing the overall performance of the DRAM-CAM system.

At block 506, the DRAM-CAM system receives query data with search criteria to identify elements within the first data. The query data can include information such as keywords, phrases, or patterns to be identified within the first data. For example, if the first data includes image data, the query data might include specific features or patterns related to the images. Alternatively, if the first data includes text data, the query data might include specific words, phrases, or text patterns. An example of a query can include searching for instances of a particular keyword or phrase in a large text document or identifying specific patterns or objects within an image dataset.

In some cases, the DRAM-CAM system can process the query data to facilitate efficient searching of the second data. For example, the DRAM-CAM system can determine appropriate search criteria (e.g., selecting relevant keywords, phrases, or patterns). As another example, in some cases, the query data can be transformed into a format compatible with the predefined format, which can enable efficient pattern matching and searching within the DRAM-CAM memory array. The processed query data can be used to perform pattern matching, identifying occurrences of elements defined by the set of search criteria.

At block 508, the DRAM-CAM system determines an available column in the second group of columns to store query indications. An available column can refer to a null or empty column, or a bit line, in each of the second groups of columns that has not yet been used for storing query data. Identifying an available column for storing query indications can ensure that the query data can be loaded into the memory array and used for pattern matching. In some cases, to determine an available column, the DRAM-CAM system determines the next column in the second group of columns that has not yet been used for storing query data. In some cases, such as in situations where all columns in the second group are occupied with query data, the DRAM-CAM system may choose to overwrite existing query data in a column. For example, the DRAM-CAM system can take into consideration factors such as the age or relevance of the existing data. As another example, the DRAM-CAM system may dynamically create additional columns to accommodate new query data. For example, the DRAM-CAM system can dynamically adjusting the number of null columns in the second group based on the characteristics of the first data and the query requirements, thereby allowing for flexible and efficient use of the memory array in the DRAM-CAM architecture. In some cases, this dynamic adjustment can be performed by monitoring the usage of the columns in the second group and resizing the second group as needed, ensuring that there is adequate space for storing query indications and optimizing the available memory resources to suit the specific needs of the DRAM-CAM system.

At block 510, the DRAM-CAM system loads query data into the available column of each of the second groups. The loading process can include transferring the query data, which may be in the form of binary or other suitable representations, into the available column that was identified in block 508. By loading the query data into the available columns, the DRAM-CAM system can utilize the memory array for efficient pattern matching and data searching operations, as the query data can be located in close proximity to the corresponding first data in the interleaved column arrangement.

In some cases, loading query data can include adjusting an organization of the first data based on the query data. For example, the DRAM-CAM system can reorganize or reorder the columns within the first group of columns to align more closely with the structure of the query data, thus facilitating faster and more efficient searching and comparison operations. The organization adjustment can be performed dynamically as new query data is introduced or as the structure of the first data changes, maintaining the optimal layout for the DRAM-CAM system's search and pattern matching processes.

At block 512, the DRAM-CAM system performs pattern matching on the first data using comparison techniques. In some cases, the comparison techniques include bit-by-bit (also referred to as bit-serial) approaches. For example, the pattern matching process can include sequentially providing rows of bits stored in the memory cells and bits of a query to a plurality of matching circuits coupled to respective bit lines associated with the columns. The pattern matching can be performed concurrently on the first groups of columns using a digital circuit that compares the first groups of columns and the available columns bit by bit. Alternatively, in some cases, the comparison techniques include bit-parallel approaches.

During the pattern matching, a count of pattern matches and corresponding locations within the memory array can be accumulated. In some cases, the pattern matching process is performed by a pattern matching engine implemented in hardware. A hardware-based approach can provide increased performance and efficiency. The hardware implementation can be tailored to the specific comparison technique used, either bit-serial or bit-parallel, further optimizing the pattern matching process.

In some cases, the DRAM-CAM system can implement chip-level parallelism within the DRAM-CAM architecture. The chip-level parallelism can enable concurrent processing across multiple sub-arrays of the memory chip, enhancing pattern matching performance and improving overall system efficiency. For example, a DRAM-CAM system with multiple memory sub-arrays can process different portions of the first data concurrently, leading to a faster identification of matching patterns and reduced latency in retrieving results.

In some cases, the DRAM-CAM system can include a plurality of memory cells addressable as rows and columns. These memory cells can be part of a DRAM subarray or bank. The DRAM-CAM system can include a plurality of matching circuits, which can be configured to be coupled to respective bit lines associated with the columns. A control circuit can be in place to store respective reference sequences in the respective columns, sequentially provide rows of bits stored in the memory cells and bits of a query to the matching circuits, and identify one of the reference sequences as corresponding to the query responsive to comparisons by the matching circuits.

In some cases, each matching circuit can include an XNOR gate with a first input that receives column entries and a second input that receives bits of the query; an AND gate having a first input coupled to an output of the XNOR gate; and a latch having an input coupled to an output of the AND gate and an output coupled to a second input of the AND gate. The control circuit can terminate the provision of rows to the matching circuits responsive to the matching circuits indicating that all of the reference sequences lack at least one bit of the query.

The DRAM-CAM system can include segment evaluation circuits coupled to respective groups of the matching circuits, which generate respective match indicators for respective subgroups of each row of bits provided to the matching circuits. Each segment evaluation circuit can include a plurality of cascaded OR gates that receive inputs from respective ones of the matching circuits and a segment register that receives and stores a value output from the plurality of cascaded OR gates and provides the stored output to another one of the segment evaluation circuits. The control circuit can latch values in the segment registers of the segment evaluation circuits during each cycle of a sequence of cycles in which the rows are provided to the matching circuits.

In some cases, the DRAM-CAM system can include secondary segment registers, which receive and store the values received and stored by respective ones of the segment registers. The control circuit can identify a column including a reference sequence corresponding to the query responsive to the secondary segment registers. The reference sequences can include respective binary-encoded k-mer patterns.

At block 514, the DRAM-CAM system outputs results of the pattern matching process. The results can include a count and the location of each element identified in the second data. These results can provide valuable information regarding the elements specified in the search criteria and their occurrences within the first data. For example, if the first data can include a large text document and the query data specifies a particular word or phrase, the results may indicate the number of occurrences of the word or phrase and their respective positions within the document. In the case of image data, the results may detail the locations of specific features or objects within the image based on the query data.

In some cases, determining or outputting can include using an aggregation system implemented in hardware to accumulate the count of pattern matches. The aggregation system can be configured as a Lookup Table (LUT) without pipeline, a LUT with pipeline, or a compressor tree. By utilizing hardware-based aggregation systems, the DRAM-CAM system can improve the efficiency and accuracy of the pattern matching results. For instance, a LUT without pipeline might be suitable for smaller datasets with fewer matches, while a LUT with pipeline or a compressor tree could handle larger datasets and more complex matching patterns, providing faster and more accurate results.

Terminology

Computer programs typically include one or more instructions set at various times in various memory devices of a computing device, which, when read and executed by at least one processor, will cause a computing device to execute functions involving the disclosed techniques. In some embodiments, a carrier including the aforementioned computer program product is provided. The carrier is one of an electronic signal, an optical signal, a radio signal, or a non-transitory computer-readable storage medium.

Any or all of the features and functions described above can be combined with each other, except to the extent it may be otherwise stated above or to the extent that any such embodiments may be incompatible by virtue of their function or structure, as will be apparent to persons of ordinary skill in the art. Unless contrary to physical possibility, it is envisioned that (i) the methods/steps described herein may be performed in any sequence and/or in any combination, and (ii) the components of respective embodiments may be combined in any manner.

Although the subject matter has been described in language specific to structural features and/or acts, it is to be understood that the subject matter defined in the appended claims is not necessarily limited to the specific features or acts described above. Rather, the specific features and acts described above are disclosed as examples of implementing the claims, and other equivalent features and acts are intended to be within the scope of the claims.

Conditional language, such as, among others, "can," "could," "might," or "may," unless specifically stated otherwise, or otherwise understood within the context as used, is generally intended to convey that certain embodiments include, while other embodiments do not include, certain features, elements and/or steps. Thus, such conditional language is not generally intended to imply that features, elements and/or steps are in any way required for one or more embodiments or that one or more embodiments necessarily include logic for deciding, with or without user input or prompting, whether these features, elements and/or steps are included or are to be performed in any particular embodiment.

Unless the context clearly can include otherwise, throughout the description and the claims, the words "include," "comprising," and the like are to be construed in an inclusive sense, as opposed to an exclusive or exhaustive sense, e.g., in the sense of "including, but not limited to." As used herein, the terms "connected," "coupled," or any variant thereof means any connection or coupling, either direct or indirect, between two or more elements; the coupling or connection between the elements can be physical, logical, or a combination thereof. Additionally, the words "herein," "above," "below," and words of similar import, when used in this application, refer to this application as a whole and not to any particular portions of this application. Where the context permits, words using the singular or plural number may also include the plural or singular number respectively. The word "or" in reference to a list of two or more items, covers all of the following interpretations of the word: any one of the items in the list, all of the items in the list, and any combination of the items in the list. Likewise the term "and/or" in reference to a list of two or more items, covers all of the following interpretations of the word: any one of the items in the list, all of the items in the list, and any combination of the items in the list.

Conjunctive language such as the phrase "at least one of X, Y and Z," unless specifically stated otherwise, is otherwise understood with the context as used in general to convey that an item, term, etc. may be either X, Y or Z, or any combination thereof. Thus, such conjunctive language is not generally intended to imply that certain embodiments require at least one of X, at least one of Y and at least one of Z to each be present. Further, use of the phrase "at least one of X, Y or Z" as used in general is to convey that an item, term, etc. may be either X, Y or Z, or any combination thereof.

In some embodiments, certain operations, acts, events, or functions of any of the algorithms described herein can be performed in a different sequence, can be added, merged, or left out altogether (e.g., not all are necessary for the practice of the algorithms). In certain embodiments, operations, acts, functions, or events can be performed concurrently, e.g., through multi-threaded processing, interrupt processing, or multiple processors or processor cores or on other parallel architectures, rather than sequentially.

Systems and modules described herein may include software, firmware, hardware, or any combination(s) of software, firmware, or hardware suitable for the purposes described. Software and other modules may reside and execute on servers, workstations, personal computers, computerized tablets, PDAs, and other computing devices suitable for the purposes described herein. Software and other modules may be accessible via local computer memory, via a network, via a browser, or via other means suitable for the purposes described herein. Data structures described herein may include computer files, variables, programming arrays, programming structures, or any electronic information storage schemes or methods, or any combinations thereof, suitable for the purposes described herein. User interface elements described herein may include elements from graphical user interfaces, interactive voice response, command line interfaces, and other suitable interfaces.

Further, processing of the various components of the illustrated systems can be distributed across multiple machines, networks, and other computing resources. In certain embodiments, one or more of the components described herein can be implemented in a remote distributed computing system. In this context, a remote distributed computing system or cloud-based service can refer to a service hosted by one more computing resources that are accessible to end users over a network, for example, by using a web browser or other application on a client device to interface with the remote computing resources.

When implemented as a cloud-based service, various components described herein can be implemented using containerization or operating-system-level virtualization, or other virtualization technique. For example, one or more components can be implemented as separate software containers or container instances. Each container instance can have certain resources (e.g., memory, processor, etc.) of the underlying host computing system assigned to it, but may share the same operating system and may use the operating system's system call interface. Each container may provide an isolated execution environment on the host system, such as by providing a memory space of the host system that is logically isolated from memory space of other containers. Further, each container may run the same or different computer applications concurrently or separately, and may interact with each other. Although reference is made herein to containerization and container instances, it will be understood that other virtualization techniques can be used. For example, the components can be implemented using virtual machines using full virtualization or paravirtualization, etc. Thus, where reference is made to "containerized" components, it should be understood that such components may additionally or alternatively be implemented in other isolated execution environments, such as a virtual machine environment.

Likewise, the data repositories shown can represent physical and/or logical data storage, including, e.g., storage area networks or other distributed storage systems. Moreover, in some embodiments the connections between the components shown represent possible paths of data flow, rather than actual connections between hardware. While some examples of possible connections are shown, any of the subset of the components shown can communicate with any other subset of components in various implementations.

Embodiments are also described above with reference to flow chart illustrations and/or block diagrams of methods, apparatus (systems) and computer program products. Each block of the flow chart illustrations and/or block diagrams, and combinations of blocks in the flow chart illustrations and/or block diagrams, may be implemented by computer program instructions. Such instructions may be provided to a processor of a general purpose computer, special purpose computer, specially-equipped computer (e.g., comprising a high-performance database server, a graphics subsystem, etc.) or other programmable data processing apparatus to produce a machine, such that the instructions, which execute via the processor(s) of the computer or other programmable data processing apparatus, create means for implementing the acts specified in the flow chart and/or block diagram block or blocks. These computer program instructions may also be stored in a non-transitory computer-readable memory that can direct a computer or other programmable data processing apparatus to operate in a particular manner, such that the instructions stored in the computer-readable memory produce an article of manufacture including instruction means which implement the acts specified in the flow chart and/or block diagram block or blocks. The computer program instructions may also be loaded to a computing device or other programmable data processing apparatus to cause operations to be performed on the computing device or other programmable apparatus to produce a computer implemented process such that the instructions which execute on the computing device or other programmable apparatus provide steps for implementing the acts specified in the flow chart and/or block diagram block or blocks.

Any patents and applications and other references noted above, including any that may be listed in accompanying filing papers, are incorporated herein by reference. Aspects of the invention can be modified, if necessary, to employ the systems, functions, and concepts of the various references described above to provide yet further implementations of the invention. These and other changes can be made to the invention in light of the above Detailed Description. While the above description describes certain examples of the invention, and describes the best mode contemplated, no matter how detailed the above appears in text, the invention can be practiced in many ways. Details of the system may vary considerably in its specific implementation, while still being encompassed by the invention disclosed herein. As noted above, particular terminology used when describing certain features or aspects of the invention should not be taken to imply that the terminology is being redefined herein to be restricted to any specific characteristics, features, or aspects of the invention with which that terminology is associated. In general, the terms used in the following claims should not be construed to limit the invention to the specific examples disclosed in the specification, unless the above Detailed Description section explicitly defines such terms. Accordingly, the actual scope of the invention encompasses not only the disclosed examples, but also all equivalent ways of practicing or implementing the invention under the claims.

To reduce the number of claims, certain aspects of the invention are presented below in certain claim forms, but the applicant contemplates other aspects of the invention in any number of claim forms. Any claims intended to be treated under 35 U.S.C. § 112(f) will begin with the words "means for," but use of the term "for" in any other context is not intended to invoke treatment under 35 U.S.C. § 112(f). Accordingly, the applicant reserves the right to pursue additional claims after filing this application, in either this application or in a continuing application.

What is claimed is:

1. A method for processing data using a DRAM-based content-addressable memory (DRAM-CAM) architecture, the method comprising:
   obtaining first data, the first data comprising at least one of text or image information, and being organized into a plurality of blocks, each block comprising a plurality of rows;
   storing the first data in a memory array of a DRAM-CAM architecture;
   converting the first data into a predefined format to form second data, the predefined format characterized by a plurality of columns arranged in an alternating pattern between first groups of columns and seconds group of columns, wherein each first group of columns corresponds to one or more rows of the plurality of rows of the first data, and wherein each second group of columns includes a predetermined number of null columns, wherein the converting comprises, for each block of the plurality of blocks of the first data:
   transforming each row of the plurality of rows of the block into one or more columns of the first groups of columns, and
   interlacing the first groups of columns with the second group of columns to produce a set of interleaved columns in the second format for the block,
   receiving a query, wherein the query indicates a set of search criteria that defines the first data as data to be searched and defines elements to be identified within the first data;
   determining an available column of the second groups of columns, wherein the available column is a null column in each of the second groups of columns;
   loading raw query data into the available column of each second group of the second groups;
   performing pattern matching on the second data to identify occurrences of elements defined by the set of search criteria, wherein the pattern matching is performed concurrently on the first groups of columns using a digital circuit that compares the first groups of columns and the available columns bit by bit, wherein the pattern matching includes accumulating a count of pattern matches and corresponding locations within the memory array; and
   outputting results of the pattern matching, wherein the results include the count and the location of each element identified in the second data.

2. A method for processing data using a DRAM-based content-addressable memory (DRAM-CAM) architecture, the method comprising:
   obtaining first data, the first data comprising at least one of text or image information, and being organized into a plurality of blocks, each block comprising a plurality of rows;
   storing the first data in a memory array of a DRAM-CAM architecture;
   converting the first data into a predefined format to form second data, the predefined format characterized by a plurality of columns arranged in an alternating pattern between first groups of columns and seconds group of columns, wherein each first group of columns corresponds to one or more rows of the plurality of rows of the first data, and wherein each second group of columns includes a number of null columns, wherein the reorganizing comprises, for each block of the plurality of blocks of the first data:
   transforming each row of the plurality of rows of the block into one or more columns of the first groups of columns, and
   interlacing the first groups of columns with the second group of columns to produce a set of interleaved columns in the second format for the block,
   wherein the second data is searchable responsive to a query.

3. The method of claim 2, wherein the number of null columns in each second group of columns is equal to or greater than a number of columns in each first group of columns.

4. The method of claim 2, wherein the number of null columns in each second group of columns is adjustable based on characteristics of the first data, and wherein the converting comprises dynamically adjusting the number of null columns based on the characteristics of the first data.

5. The method of claim 2, wherein at least one of a size or the number of null columns in each second group of columns is based on timing parameters associated with the DRAM-CAM architecture.

6. The method of claim 2, wherein said converting the first data into the predefined format is performed by a hardware data transposition unit implemented in hardware.

7. A method for searching data in a DRAM-based content-addressable memory (DRAM-CAM) architecture, the method comprising:
   receiving a query, wherein the query indicates a set of search criteria that defines first data as data to be searched and defines elements to be identified within the first data;
   loading query data into an available column of each second group of columns, wherein the available column is a null column in each of the second groups of columns, wherein the second groups of columns are stored alongside first groups in an alternating pattern between the first groups of columns and the seconds group of columns, wherein the first group of columns corresponds to reference data to be searched;

performing pattern matching on the first data to identify occurrences of elements defined by the set of search criteria, wherein the pattern matching includes accumulating a count of pattern matches and corresponding locations within the memory architecture; and outputting results of the pattern matching.

8. The method of claim 7, wherein the available column for storing query indications is located in a same position in each of the second groups of columns.

9. The method of claim 7, wherein the pattern matching is performed concurrently on the first groups of columns using a digital circuit that compares the first groups of columns and the available columns bit by bit.

10. The method of claim 7, wherein the pattern matching is performed concurrently on the first groups of columns using a digital circuit that compares the first groups of columns and the available columns in a bit-parallel manner.

11. The method of claim 7, further comprising determining the available column of the second groups of columns.

12. The method of claim 7, wherein the results include the count and the location of each element identified in the first data.

13. The method of claim 7, wherein said performing pattern matching is performed by a pattern matching engine implemented in hardware.

14. The method of claim 7, wherein said accumulating the count is performed by an aggregation system implemented in hardware, wherein the aggregation system is configured as a Lookup Table (LUT) without pipeline, a LUT with pipeline, or a compressor tree.

15. The method of claim 7, wherein chip-level parallelism is implemented within the DRAM-CAM architecture, the chip-level parallelism enabling concurrent processing across multiple sub arrays of a memory chip to enhance pattern matching performance.

16. The method of claim 7, wherein the pattern matching is performed on a text file using a set of search patterns including unique words, and the method further comprises aggregating hits for each input word within the memory array.

17. The method of claim 7, further comprising:
detecting that all available columns in the second group of columns are occupied, and
designating a column within the second group of columns for overwriting, wherein the designated column is the available column.

18. The method of claim 7, wherein the pattern matching is performed on an image file using a set of search patterns including 8-bit pixel patterns, and the method further comprises aggregating hits for each pixel pattern within the memory array.

19. The method of claim 7, wherein the pattern matching further comprises masking certain columns of the first data to selectively search for the elements.

* * * * *